United States Patent
Trau et al.

(10) Patent No.: US 11,744,489 B2
(45) Date of Patent: Sep. 5, 2023

(54) NONINVASIVE OPTICAL SENSOR FOR ANALYZING A LEVEL OF A SUBSTANCE IN A SUBJECT BY ILLUMINATING THE SCLERA

(71) Applicant: NATIONAL UNIVERSITY OF SINGAPORE, Singapore (SG)

(72) Inventors: Dieter Wilheim Trau, Singapore (SG); Shihao Li, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 712 days.

(21) Appl. No.: 16/612,762

(22) PCT Filed: May 11, 2018

(86) PCT No.: PCT/SG2018/050230
§ 371 (c)(1),
(2) Date: Nov. 12, 2019

(87) PCT Pub. No.: WO2018/208233
PCT Pub. Date: Nov. 15, 2018

(65) Prior Publication Data
US 2020/0163593 A1    May 28, 2020

(30) Foreign Application Priority Data
May 12, 2017    (SG) ............................ 10201703893V

(51) Int. Cl.
*A61B 5/1455*    (2006.01)
*A61B 3/00*    (2006.01)
*A61B 5/103*    (2006.01)

(52) U.S. Cl.
CPC .......... *A61B 5/1455* (2013.01); *A61B 3/0008* (2013.01); *A61B 5/1032* (2013.01)

(58) Field of Classification Search
CPC .... A61B 5/1032; A61B 5/1455; A61B 5/1495
See application file for complete search history.

(56) References Cited

U.S. PATENT DOCUMENTS

| | | | |
|---|---|---|---|
| 6,045,502 A | 4/2000 | Eppstein et al. | |
| 2006/0094942 A1* | 5/2006 | Winther | A61B 5/14558 600/319 |
| 2014/0176693 A1* | 6/2014 | Podoleanu | G02B 21/0056 348/78 |

FOREIGN PATENT DOCUMENTS

| CN | 101031232 A | * | 9/2007 | .......... A61B 5/0071 |
|---|---|---|---|---|
| CN | 201806696 U | * | 4/2011 | |

(Continued)

OTHER PUBLICATIONS

Naveen Balasubramanian, "Spectrophotometric Quantification of Bilirubin in Sclera of the Eye Using Visible DLP® Hyperspectral Imaging", May 2012 (Year: 2012).*

(Continued)

*Primary Examiner* — Maurice C Smith
(74) *Attorney, Agent, or Firm* — SOROKER AGMON NORDMAN PTE LTD

(57) ABSTRACT

A noninvasive optical sensor for analyzing a level of a substance in a subject by illuminating a sclera may include at least one light source, at least one detector, and a processor. The at least one light source may direct incident light to illuminate a region of the sclera of an eye of the subject. The at least one detector may receive light, in response to the incident light, from the sclera or from inside the eye proximal to the illuminated region of the sclera. The processor may be configured to compute a ratio of an intensity of the received light from the at least one detector to a reference value and to estimate a level of a substance in the subject from the computed ratio.

17 Claims, 9 Drawing Sheets

(56) References Cited

FOREIGN PATENT DOCUMENTS

| | | | | | |
|---|---|---|---|---|---|
| CN | 103188993 | A | * | 7/2013 | ........... A61B 3/1173 |
| CN | 105943056 | A | * | 9/2016 | |
| CN | 106214126 | A | | 12/2016 | |
| JP | 2003532461 | A | * | 11/2003 | |
| RU | 2007141468 | A | | 5/2009 | |
| WO | 0178589 | A1 | | 10/2001 | |
| WO | WO-2004112601 | A1 | * | 12/2004 | ............... A61B 3/10 |
| WO | 2014181744 | A1 | | 11/2014 | |
| WO | 20151183994 | A1 | | 12/2015 | |

OTHER PUBLICATIONS

Balasubramanian, N.B. MSc Thesis. Spectrophotometric Quantification of Bilirubin in Sclera of the Eye Using Visible DLP® Hyperspectral Imaging. Jun. 25, 2012.

Cu, A. et al., Fluorescence of bilirubin. J. Am. Chem. Soc., Apr. 1975, vol. 97, No. 9, pp. 2579-2580.

Lamola, A.A. and Russo, M., Fluorescence Excitation Spectrum of Bilirubin in Blood: A Model for the Action Spectrum for Phototherapy of Neonatal Jaundice. Photochem Photobiol. , Dec. 10, 2013, vol. 90, No. 2, pp. 294-296.

\* cited by examiner

NONINVASIVE OPTICAL SENSOR FOR ANALYZING A LEVEL OF A SUBSTANCE IN A SUBJECT BY ILLUMINATING THE SCLERA

TECHNICAL FIELD

The present disclosure generally relates to a noninvasive optical sensor, and more specifically to a method and apparatus for analyzing a level of a substance in a subject by illuminating the subject's sclera. The noninvasive optical sensor and method may be applied in (point of care) diagnostics and theragnostics for human beings and animals, as well as analyzing drug delivery, pharmacokinetic and pharmacodynamnic properties of a drug and a drug candidate.

BACKGROUND

Jaundice is a medical condition caused by the dysfunction of the liver to remove bilirubin from the body. Accumulation of bilirubin leads to yellow coloring of the skin, the gums, and the sclera of a subject due to high levels of bilirubin in the subject. Left untreated, the medical dysfunctions causing jaundice may be fatal in adults and/or may cause brain damage in neonatals. Jaundice screening of a subject such as in an adult or infants during neonatal care may be performed by invasive blood tests to detect bilirubin levels in the blood of the subject.

Jaundice may also be detected by noninvasive methods by analyzing the skin color of a subject by visual means or by using an apparatus. Analysis by visual means is qualitative and subjected to the skills of the health professional. Analysis using an apparatus can be performed by reflection photometry or imaging. Transcutaneous jaundice meters typically use reflection photometry and used typically on the forehead to measure bilirubin levels. Imaging the body of the subject, pixelating the image, and counting for example, the number of yellow pixels in the image can be used to determine the extent of jaundice.

The problem with all noninvasive approaches is that analyzing or imaging the color of the skin is affected by the subjects' skin pigmentation such as melanin, which may affect the determination of the extent of jaundice.

Thus, there is a need for more accurate noninvasive methods that is not affected by the different skin pigmentation of subjects for accurate jaundice diagnosis in a subject.

SUMMARY

The current disclosure provides a solution for the problem of inaccurate measurements by transcutaneous jaundice meters caused by skin pigmentation and adipose tissue under the skin. Instead of analyzing jaundice by measurements on skin, the current disclosures analyses the sclera of a subject. Advantageously, such measurements are not affected by skin pigmentation and adipose tissue, and provide more accurate measurements.

There is thus provided, in accordance with some embodiments of the present disclosure, a noninvasive optical sensor device for analyzing a level of a substance in a subject by illuminating a sclera, the optical sensor may include at least one light source, at least one detector, and a processor. The at least one light source may direct incident light to illuminate a region of a sclera of an eye of a subject. The at least one detector may receive light, in response to the incident light, from the sclera or from inside the eye proximal to the illuminated region of the sclera. The processor may be configured to compute a ratio of an intensity of the received light from the at least one detector to a reference value and to analyze a level of a substance of the subject from the computed ratio.

Furthermore, in accordance with some embodiments of the present disclosure, the received light may include reflected light, or scattered light, or fluorescent light, or a mixture thereof from the sclera or from inside the eye proximal to the illuminated region of the sclera.

Furthermore, in accordance with some embodiments of the present disclosure, the received light may include light emitted by fluorescence from tissue or fluorescent chemical entities excited by the incident light from the sclera or from inside the eye proximal to the illuminated region of the sclera.

Furthermore, in accordance with some embodiments of the present disclosure, the level of the substance may be the level of the substance in the blood of the subject.

Furthermore, in accordance with some embodiments of the present disclosure, the optical sensor device may include optics for focusing the incident light onto the region of the sclera.

Furthermore, in accordance with some embodiments of the present disclosure, the optics may be configured to autofocus the incident light onto the region of the sclera.

Furthermore, in accordance with some embodiments of the present disclosure, the optical sensor device may include a communication module for relaying data to a remote communication device.

Furthermore, in accordance with some embodiments of the present disclosure, the communication module may include a Bluetooth module or a Wireless Fidelity (WiFi) module.

Furthermore, in accordance with some embodiments of the present disclosure, the processor is located on the remote mobile device and may be configured to use the relayed data so as to compute the ratio on the remote communication device.

Furthermore, in accordance with some embodiments of the present disclosure, the at least one light source may be selected from the group consisting of a xenon flash lamp, a light emitting diode, a laser diode, and a polychromatic light source with a bandpass filter.

Furthermore, in accordance with some embodiments of the present disclosure, the at least one detector may be selected from the group consisting of a photodiode, a photomultiplier tube, a photoresistor, a charge coupled device (CCD) sensor, a complementary metal-oxide semiconductor (CMOS) sensor, a fluorescence detector, a filtered photodiode, a spectrometer, and a camera.

Furthermore, in accordance with some embodiments of the present disclosure, the at least one light source emits pulsed light.

Furthermore, in accordance with some embodiments of the present disclosure, the at least one light source emits pulsed light to enable the method of time resolved fluorescence. A short light pulse is used to excite a fluorophore and the decaying fluorescence emission is detected by the at least one detector.

Furthermore, in accordance with some embodiments of the present disclosure, the level of the substance may include the concentration level of bilirubin in the blood.

Furthermore, in accordance with some embodiments of the present disclosure, the incident light directed to the region of the sclera for analyzing the concentration level of bilirubin may include light from the at least one light source with optical wavelengths in a range of 400 nm to 500 nm.

The other incident light directed to the region of the sclera for the purpose of reference and normalization of the signal for analyzing the concentration level of bilirubin, may include light from the at least one light source with optical wavelengths out of the range of 400 nm to 500 nm. The received light in the at least one detector may include reflected light and scattered light from the eye in said range.

Furthermore, in accordance with some embodiments of the present disclosure, the incident light directed to the region of the sclera for analyzing the concentration level of bilirubin may include light from the at least one light source with optical wavelengths in a range of 380 nm to 500 nm. The other incident light directed to the region of the sclera for the purpose of reference and normalization of the signal for analyzing the concentration level of bilirubin, may include light from the at least one light source with optical wavelengths out of the range of 380 am to 500 nm. The received light in the at least one detector may include florescent light emitted from the eye above 500 nm.

Furthermore, in accordance with some embodiments of the present disclosure, the processor may be configured to assess that the subject has jaundice when the analyzed concentration level of bilirubin in the blood exceeds a predefined threshold.

Furthermore, in accordance with some embodiments of the present disclosure, the incident light directed to the region of the sclera for analyzing the concentration level of a substance may start from the UV at 250 nm to the near Infrared at 800 nm and the received light in the at least one detector may include fluorescent light emitted from the eye a range of 350 nm to 1000 nm. Light pulses with pulse lengths ranging from femtoseconds to seconds may be applied to control the amount of the light entering into eyes.

Furthermore, in accordance with some embodiments of the present disclosure, the noninvasive optical sensor and method may be applied in (point of care) diagnostics and theragnostics for human beings and animals.

Furthermore, in accordance with some embodiments of the present disclosure, the incident light directed to the region of the sclera and other regions (e.g. iris and pupil) may be used for analyzing drug delivery, pharmacokinetic and pharmacodynamic properties of a drug and a drug candidate may include the light from the at least one light source with optical wavelengths in a range of the excitation wavelengths of an inherently fluorescent drug (candidate), e.g. OsteoSense750/OsteoSense680 (bone targeting), or in a range of the excitation wavelengths of the fluorophore conjugated drug (candidate), e.g. Trastuzmab-Alexa750 (cancer targeting). The other incident light directed to the region of the sclera for the purpose of reference and normalization may include light from the at least one light source with optical wavelengths out of the said range.

Furthermore, in accordance with some embodiments of the present disclosure, the method above is not limited to analyzing a drug (candidate) level in blood, but also applies on intravitreal drug delivery and transscleral drug delivery, analyzing drug (candidate) level in the eye by measuring the fluorescence intensity.

There is further provided, in accordance with some embodiments of the present disclosure, a method for analyzing a level of a substance in the blood of a subject by illuminating a sclera with a noninvasive optical sensor device may include directing incident light from at least one light source to illuminate a region of a sclera of an eye of a subject. Light in at least one detector may be received, in response to the incident light, from the sclera or from inside the eye proximal to the illuminated region of the sclera. A ratio of an intensity of the received light from the at least one detector to a reference value may be computed. A level of a substance in the blood of the subject may be calculated from the computed ratio.

BRIEF DESCRIPTION OF THE DRAWINGS

Some non-limiting exemplary embodiments or features of the disclosed subject matter are illustrated in the following drawings.

In the drawings.

Figure 1A:
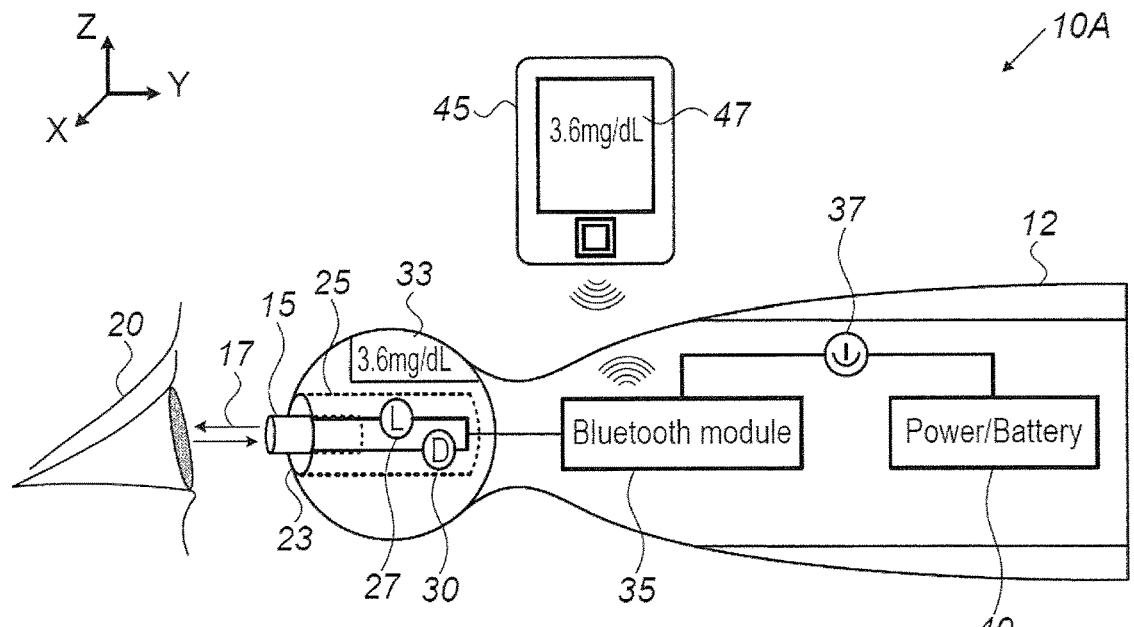
FIG. 1A illustrates a first embodiment of an optical sensor device, in accordance with some embodiments of the present disclosure.

With specific reference now to the drawings in detail, it is stressed that the particulars shown are by way of example and for purposes of illustrative discussion of embodiments of the disclosure. In this regard, the description taken with the drawings makes apparent to those skilled in the art how embodiments of the disclosure may be practiced.

Identical or duplicate or equivalent or similar structures, elements, or parts that appear in one or more drawings are generally labeled with the same reference numeral, optionally with an additional letter or letters to distinguish between similar entities or variants of entities, and may not be repeatedly labeled and/or described. References to previously presented elements are implied without necessarily further citing the drawing or description in which they appear.

Dimensions of components and features shown in the figures are chosen for convenience or clarity of presentation and are not necessarily shown to scale or true perspective. For convenience or clarity, some elements or structures are not shown or shown only partially and/or with different perspective or from different point of views.

DETAILED DESCRIPTION

The apparatus and method provided herein according to some embodiments of the present disclosure, enable the noninvasive determination of a level of a substance in the blood of a subject by the illuminating a region of a sclera of the eye of a subject. Embodiments of the optical sensor device described herein may analyze the intensity and spectrum of received light from the sclera or from inside the eye proximal to the illuminated region of the sclera, in response to illuminating the sclera, for assessing a level of a substance in the blood.

The provided system and method solves the problem of noninvasive neonatal or children jaundice screening by determining the concentration of bilirubin levels in the blood of the subject precluding the need for acquiring transcutaneous blood samples at predefined intervals. The optical probing of the sclera may provide a more accurate method for jaundice assessment, since the sclera is less influenced by other pigments in the subject, such as melanin, for example, which caused by ethnicity.

The embodiments taught herein may overcome problems of adipose tissue, which may cause either an overestimation or underestimation of bilirubin concentration levels in the blood of the subject. The embodiments taught herein may provide an early detection of jaundice, since jaundice is visible on sclera first and then followed by color changes on the skin of the subject. The embodiments taught herein may also provide the possibility of detection of adult jaundice and animal jaundice. Adult jaundice may be measured by a blood test. For animal subjects, transcutaneous bilirubin meters cannot be applied to animals due to the fur on their skin for measuring animal jaundice.

Thus, the embodiments taught herein are not limited to infants and children, but may include adults and/or animals (e.g., any living subject), for example. Furthermore, the optical probing of the sclera may not be limited for assessing concentration levels of bilirubin in the subject, but may be used for assessing any other substances in the blood such as hemoglobin and/or oxygen saturation levels, and % or a drug taken by the subject in the course of medication, and/or natural substances present in the body such as NADH/NAD, hormones, vitamins, and/or synthetic substances such as drugs, reagents, dyes, and protein aggregates occurring or building up in the eye, for example.

Furthermore, the embodiments taught herein could also apply to analyzing drug delivery, pharmacokinetic and pharmacodynamic properties of a drug and a drug candidate level in blood, also applies on intravitreal drug delivery and transscleral drug delivery, analyzing drug (candidate) level in the eye by measuring the fluorescence intensity.

FIG. 1A illustrates a first embodiment of an optical sensor device 10A, in accordance with some embodiments of the present disclosure.

Figure 1B:
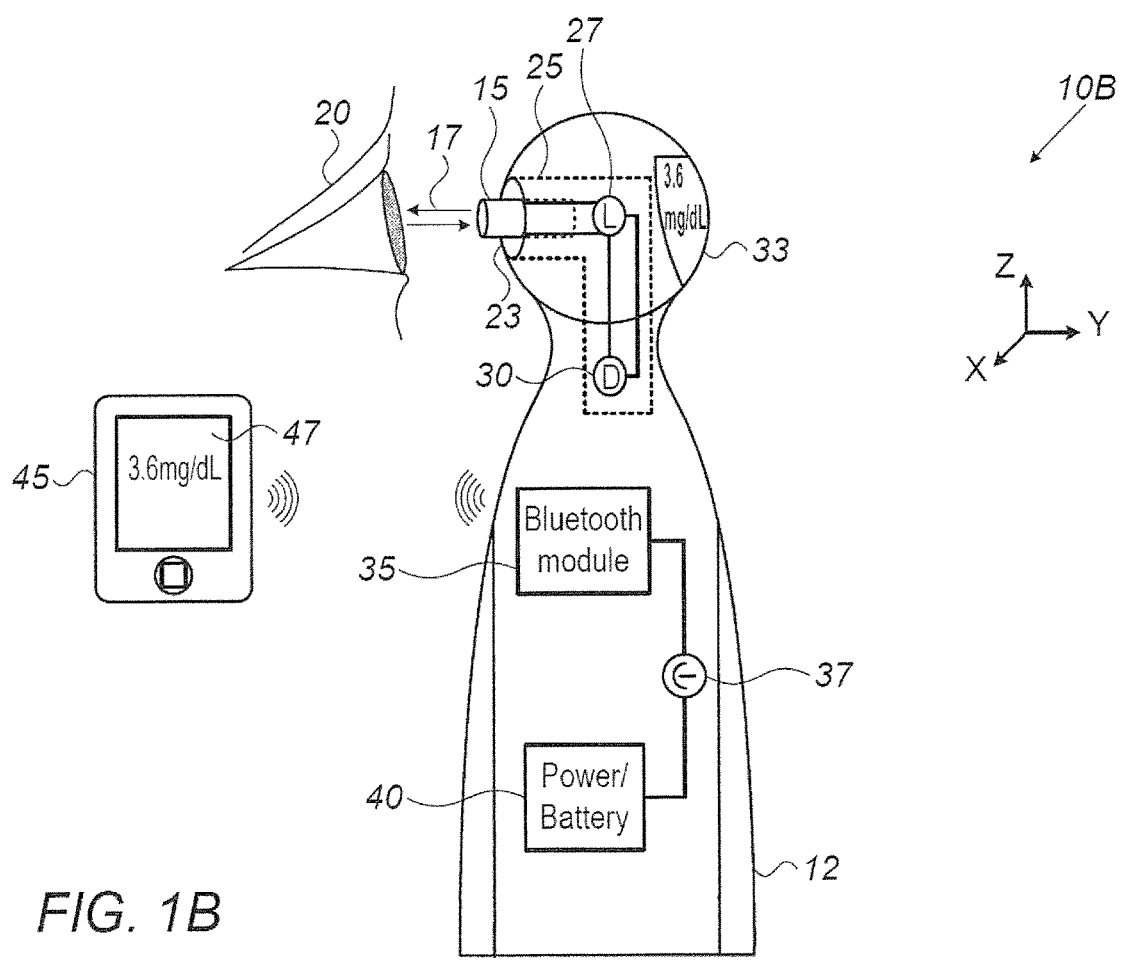
FIG. 1B illustrates a second embodiment of an optical sensor device, in accordance with some embodiments of the present disclosure.

FIG. 1B illustrates a second embodiment of an optical sensor device 10B, in accordance with some embodiments of the present disclosure.

Optical sensor device 10A and 10B may be denoted collectively herein below as optical sensor device 10. Optical sensor device 10A may include a distal end 15 for directing and receiving light to/from the sclera of an eye 20 of the subject along an optical axis 17. A housing 12 may be substantially oriented along a same axis (e.g., y-axis as the exemplary axis shown in FIG. 1A) as optical axis 17 in optical sensor device 10A. Optical sensor device 10B may include distal end 15 for directing and receiving light to/from the sclera of an eye 20 of the subject along an optical axis 17. However, housing 12 may be substantially oriented along a perpendicular axis (e.g., z-axis as the exemplary axis shown in FIG. 1B) as optical axis 17 (e.g., y-axis) in optical sensor device 10B. X-Y-Z axes are shown merely for conceptual clarity and not by way of limitation of the embodiments of the present disclosure.

Optical sensor device 10 may include an optical module 25 with at least one light source 27 and at least one detector 30. Optical module 25 may include optics and/or optical fibers to direct incident light from at least one light source 27 onto the sclera of eye 20, and to receive light from eye 20 in at least one detector 30.

Optical sensor device 10 may include housing 12 in the form factor of a handheld device. However, housing 12 may be of any suitable form factor and/or size that may be operated by a healthcare worker or doctor, for example. Optical sensor device 10 may further include a power source 40, a Bluetooth module 35, an on/off switch 37, and a monitor screen or display 47. In some embodiments, optical sensor device 10 may include an accelerometer. Display 47 may display bilirubin levels from the optical measurements.

In some embodiments of the present disclosure. Bluetooth module 35 may communicate data with optical measurements from the sclera to a remote communication device 45 including a display 47 to display bilirubin levels from the optical measurements on a mobile application.

In some embodiment of the present disclosure, the optical sensor device 10 may be attached to the communication device 45 in a way that both devices form a single unit. The attachment may be detachable.

In some embodiment of the present disclosure, optical sensor device 10 may include an autofocusing system 23. Autofocusing system may further include a proximity sensor to adjust the distance to eye 20.

Figures 2A, 2B:
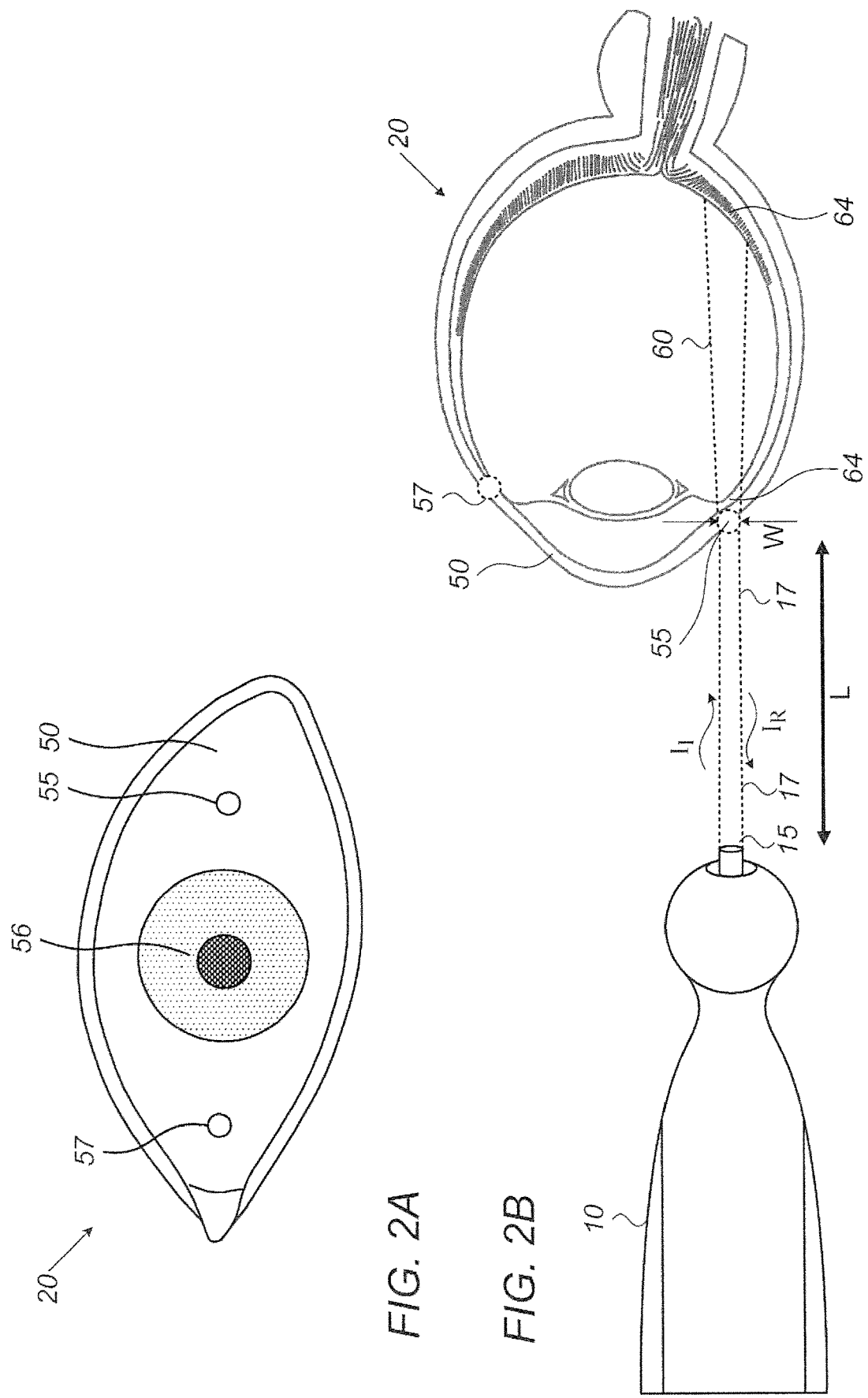
FIG. 2A schematically illustrates a front view of an eye, in accordance with some embodiments of the present disclosure.
FIG. 2B schematically illustrates a top crossectional view of an eye, in accordance with some embodiments of the present disclosure.

FIG. 2A schematically illustrates a front view of eye 20, in accordance with some embodiments of the present disclosure. FIG. 2A illustrates with a sclera 50 with two exemplary regions 55 and 57 on sclera 50 on each side of an iris 56 of eye 20.

FIG. 2B schematically illustrates a top crossectional view of eye 20, in accordance with some embodiments of the present disclosure.

Optical sensor device 10 may be used to direct incident light from at least one light source 27 with an intensity denoted L along optical axis 17 on region 55 of sclera 50. The incident light may be focused by optics to a width W on sclera 50 in region 55. Some of the incident light may pass through sclera 50 to further illuminate a second region 60 inside eye 20 proximal to the illuminated region 55 of sclera 50. Optical sensor device 10 may direct incident light to illuminate any suitable point on sclera 50, such as in region 57, for example, on the other side of iris 56, which is shown merely for visual clarity in FIG. 2A, and not by way of limitation of the embodiments of the present disclosure. Any region may be illuminated by the incident light on sclera 50. In this configuration, minimal incident light enters eye 20.

Autofocusing system 23 may be used for achieving the non-contact measurement without any facilitating accessories. A distance L to eye 20 from distal end 15 is typically 1 to 20 mm. Optical measurements may be acquired preferably about 3 to 10 mm to eye 20. Autofocusing system 23 may detect and dynamically adjust a distance L to the eye (e.g., the distance from distal end 15 to region 55). This autofocusing feature allows optical sensor device 10 to maintain a fixed distance (e.g., distance L) to eye 20 for performing non-contact and non-invasive measurements. Thus, healthcare workers may conduct the routine jaundice screening more safely.

Once distal end 15 is at the desired distance L, circuitry in optical sensor device 10 may trigger optical module 25 to acquire the optical measurements automatically by directing incident light onto sclera 50 in region 55.

In response to the incident light illuminating region 55, optical sensor device 10 may receive light with a received intensity $I_R$ in at least one detector 30. The received light may be reflected light and/or scattered light and/or fluorescent light from sclera 50 at and/or near region 55 such as in second region 60, or from fluorescence emissions from tissue 64 excited by the incident light which propagates back to optical sensor device 10 and detected in at least one detector 30.

Figure 3:
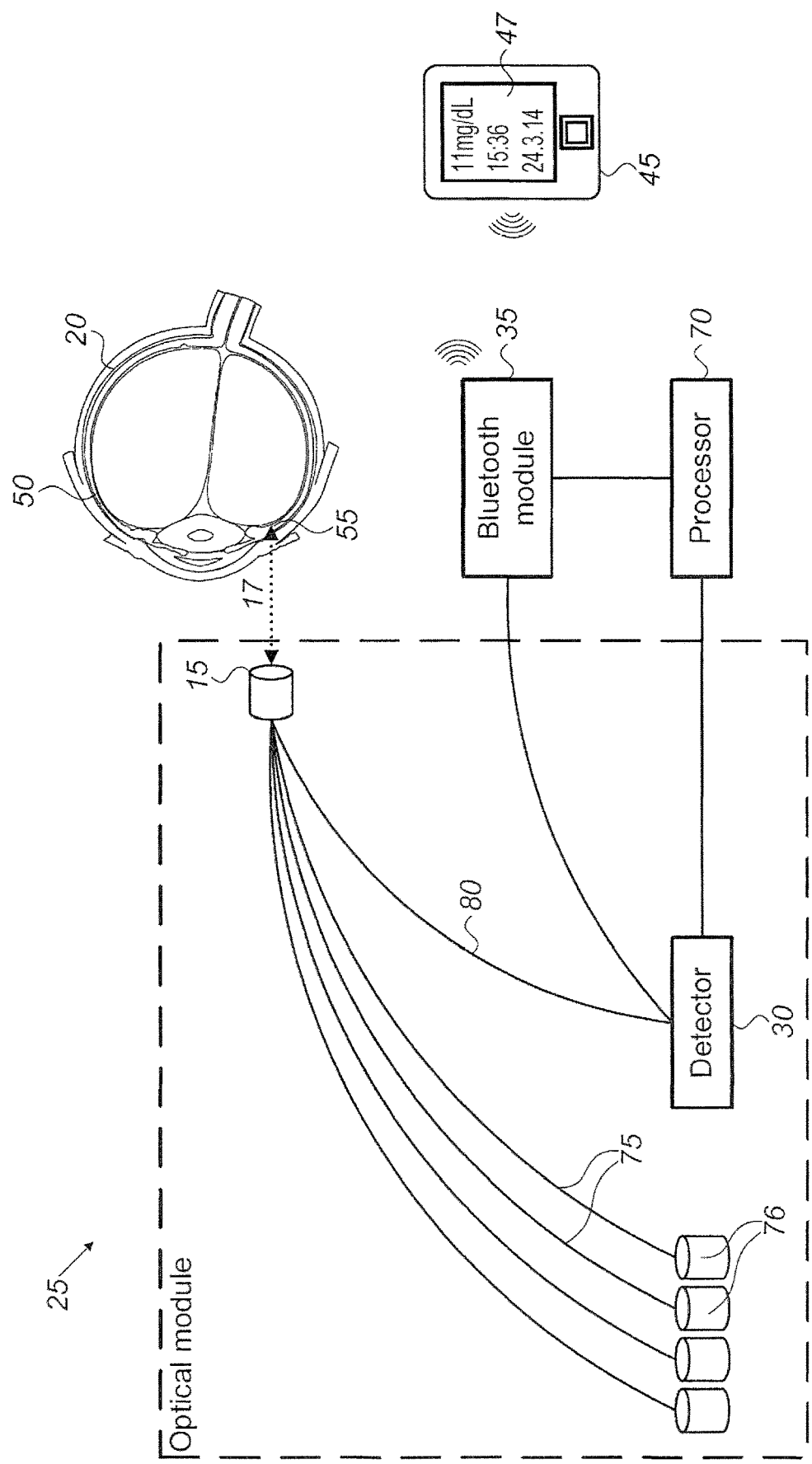
FIG. 3 schematically illustrates an optical module, in accordance with some embodiments of the present disclosure.

FIG. 3 schematically illustrates optical module 25, in accordance with some embodiments of the present disclosure. Optical module 25 may include light emitting diodes (LED) 76, detector 30, and an optical probe 77 positioned near distal end 15 in optical sensor device 10. Light from light emitting diodes (LED) 76 may be coupled to optical probe 77 via respective optical fibers 75, which directs light to region 55 of eye 20 along optical axis 17.

Similarly, optical probe 77 may receive light from the eye in response to the directed light, which may be coupled to detector 30 via an optical fiber 80. Light may be guided from light source 27 to sclera 50, and received light may be guided from sclera 50 to detector 30 with optics such as lenses and/or optical fibers.

A processor 70 may receive data from detector 30 such as the intensity of the received light and may process the data to analyze the bilirubin concentration level in the blood of the subject. Optionally and/or additionally, processor 70 may relay the data to remote communication device 45 via Bluetooth module 35. Remote communication device 45 may display bilirubin concentration level in the blood of the subject on a display 47. Any calculations of data to analyze a substance may be performed in optical sensor device 10 or in remote communication device 45, or in both.

Figure 4:
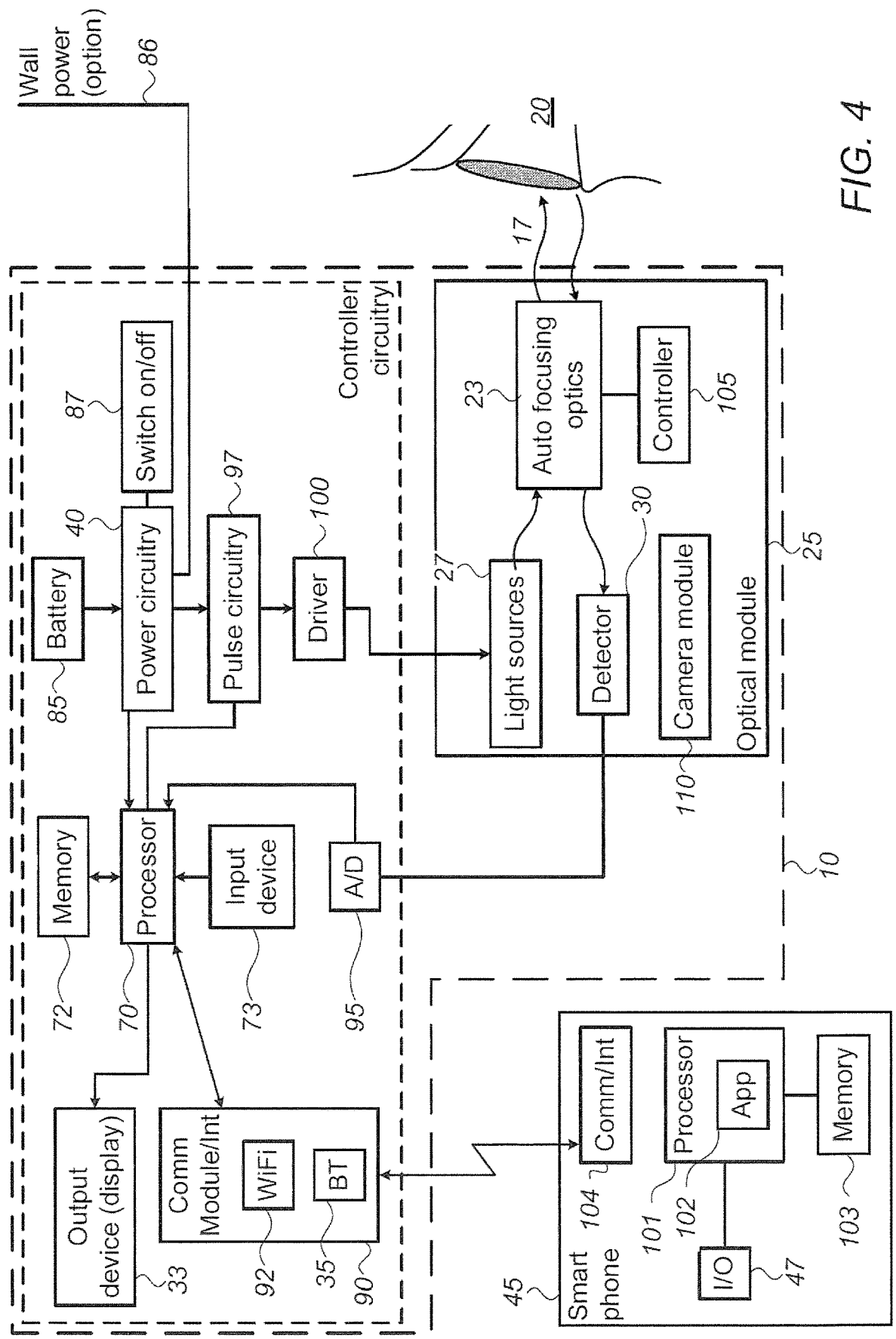
FIG. 4 schematically illustrates a block diagram of an optical sensor device, in accordance with some embodiments of the present disclosure.

FIG. 4 schematically illustrates a block diagram of optical sensor device 10, in accordance with some embodiments of the present disclosure. Optical sensor device 10 may include optical module 25 and controller circuitry 65. Optical module 25 may include light sources 27, detector 30, autofocusing system 23 controlled by a controller 105, and camera module 110. Camera module 110 may record a picture of eye 20. The picture may be used to position optical axis 17 of the light from light source 27 onto sclera 50. The picture may also be used to identify the subject (e.g., the patient).

Controller circuitry 65 may include processor 70 coupled to a memory 72, an input device 73, output device 33 (e.g., display 47 in FIGS. 1A and 1B), and a communication module and interface (CMI) 90. CMI 90 may include a wireless transmitter and/or receiver, which may select Bluetooth module 35 or a Wireless Fidelity (Wi-Fi) module 92 to communicate with remote communication device 45, such as a smartphone or a tablet device CMI 90 may communicate with another computer.

Controller circuitry 65 may include an analog-to-digital converter (A/D) 95 for converting the analog signal output from detector 30 to a digital signal coupled to processor 70.

Controller circuitry 65 may include power circuitry 40 capable of being powered by a battery 85 with an on/off power switch 87. In some embodiments, battery 85 may be charged via a micro-USB cable, for example. Additionally and/or optionally in some embodiments, optical sensor module 10 may be powered by a mains power source 86 (wall supply). Power circuitry 40 may convert the (AC) wall supply voltage to the internal voltages for charging battery 85 and powering controller circuitry 65 for applications where mobility and/or portability may be less critical.

Power circuitry 40 may be coupled to processor 70 and to drive pulse circuitry 97 controlled by processor 70. The output of pulse circuitry 97 may be used as the input to driver circuitry 100 whose output drives light source 27. Light source 27 may produce pulsed or continuous wave light signals to be directed to sclera 50 of eye 20.

Remote communication device 45 may include a processor 101, a memory 103, a communication module and interface (CMI) 104, and input/output (I/O) devices such as touch display 47. An application (APP) 102 may be executed by processor 101. APP 102 may be an IOS (Apple) or Android or PC-based application. APP 102 (e.g., processor 101) may process data received from CMI 90 via CMI 104 to compute the bilirubin concentration from the data. The concentration may be displayed on a screen, or monitor, or display on remote communication device 45. The bilirubin concentration may be displayed in any suitable units, but typically in mg/dL.

In some embodiments of the present disclosure, the data may be stored in memory 103 after being processed by APP 102, which may permit sharing patient data between doctor's offices and wards, for example, APP 102 operating on remote communication device 45 may bypass the use of a desktop or laptop computer. The user-friendly interface of APP 102 may allow easier data sharing and data collection.

Processor 70 may include one or more processing units. Processor 70 may be configured to operate in accordance with programmed instructions stored in memory 72. Processor 70 may be capable of executing an application for analyzing a level of a substance in the blood of a subject by illuminating sclera 50 using noninvasive optical sensor device 10.

Processor 70 may communicate with a screen of output device 33 to display the level of a substance in the blood of a subject. In another example, output device 33 may include a printer, display panel, speaker, or another device capable of producing visible, audible, or tactile output in embodiments where optical sensor device 10 may be coupled externally to an external computer and/or to external I/O peripheral devices. For example, in these embodiments, processor 70 may communicate with input device 73. For example, input device 73 may include one or more of a keyboard, keypad, or pointing device for enabling a user to inputting data or instructions for operation of processor 70. Optical sensor device 10 may be operated by a keyboard on the handheld device, or integrated into the handheld device. Optical sensor device 10 may be operated by an external keyboard remotely controlled via a smart phone, or tablet device, or an external computer.

Processor 70 may communicate with memory 72. Memory 72 may include one or more volatile or nonvolatile memory devices. Memory 72 may be utilized to store, for example, programmed instructions for operation of processor 70, data or parameters for use by processor 70 during operation, or results of operation of processor 70.

In operation, processor 70 and/or processor 101 may execute a method for analyzing a level of a substance in the blood of a subject by illuminating a sclera with a noninvasive optical sensor device. The calculations and/or algorithms may be performed in optical sensor device 10 (e.g., in processor 70), or in the smart phone (e.g., in processor 101 of remote communication device 45) or in tablet device, or in a computer, or in any combination of devices thereof.

In some embodiments of the present disclosure, the at least one detector may measure an ambient light signal to correct for ambient light during the measurement. Typically, the ambient light intensity may be deducted from the measurement intensity.

In some embodiments of the present disclosure, more than one reading may be taken in general to analyze bilirubin level. If the readings deviate from each other more than a predefined value of an acceptable error between measurements, optical sensor device 10 may issue a warning to the user on output device 33, for example, to repeat the procedure.

The at least one light source may include a xenon flash lamp. The at least one light source may include different single wavelength light emitting diodes (LED) operating at wavelengths of 446 nm, 486 nm, 502 nm and 531 nm, for example. The wavelength variance may be +1-20 nm of the stated wavelength. In general, the at least one light source may include LEDs operating in the wavelength range of 400 nm-500 nm, and an LED operating above 530 nm for use as a reference signal. However, any suitable LED wavelength may be used to perform the method of analyzing a level of a substance in the blood of a subject by illuminating a sclera.

The at least one light source may include monochromatic light generated by a polychromatic light source and a bandpass filter at the desired wavelength. Optionally and/or alternatively, the bandpass filter may be mounted in front of the detector to filter the received light.

Pulse circuitry 97 may permit the delivery of continuous wave (CW) light or light pulses as incident light directed to region 55 of sclera 50. Pulse circuitry 97 may generate light pulses with pulse lengths ranging from femtoseconds to seconds to control the amount of the light entering into the eyes. More than one pulse may be delivered to perform multiple measurements. Processor 70 or processor 101 may average the intensity from several light pulses. Light of different wavelengths may be selected by switching on and off the different at least one light sources each with different wavelengths, for example. Using light sources that are pulsed as described herein, a single measurement may be performed within 100 msec.

The at least one detector may be selected from, but not limited to a photodiode, photomultiplier tube, photoresistor, a charge coupled device (CCD) sensor, a complementary metal oxide semiconductor (CMOS) sensor, a fluorescence detector, a filtered photodiode, a spectrometer, a camera and/or other like devices.

Optical systems, including light sources, such as a xenon flash lamp or certain wavelengths LEDs, and a detector as described herein, allows optical sensor device 10 to be implemented as a simple and low-cost optical system, without the need for very expensive CCD camera systems.

Some embodiments of the present disclosure described herein utilize the absorption of light by bilirubin to analyze the bilirubin concentration in the blood of the subject. Incident light by the least one light source may be directed to region 55 in eye 20 and absorbed by bilirubin in the sclera and/or in blood vessels in tissue 64 of eye 20. Processor 70 and/or processor 101 may be used to comparing a ratio of the received light intensity to the incident light intensity at different wavelengths. The ratio at different wavelengths is indicative of the absorption of light by bilirubin, and may be used to analyze the bilirubin concentration in the blood of the subject.

Processor 70 and/or processor 101 may be used to assess that the subject has jaundice when the analyzed concentration level of bilirubin in the blood exceeds a predefined threshold. For example, in adults, bilirubin levels are typically below 1.0 mg/dL and levels over 2-3 mg/dL may be indicative of jaundice. Jaundice in newborn babies may be assessed when the bilirubin levels are greater than 4-21 mg/dL.

Figure 5:
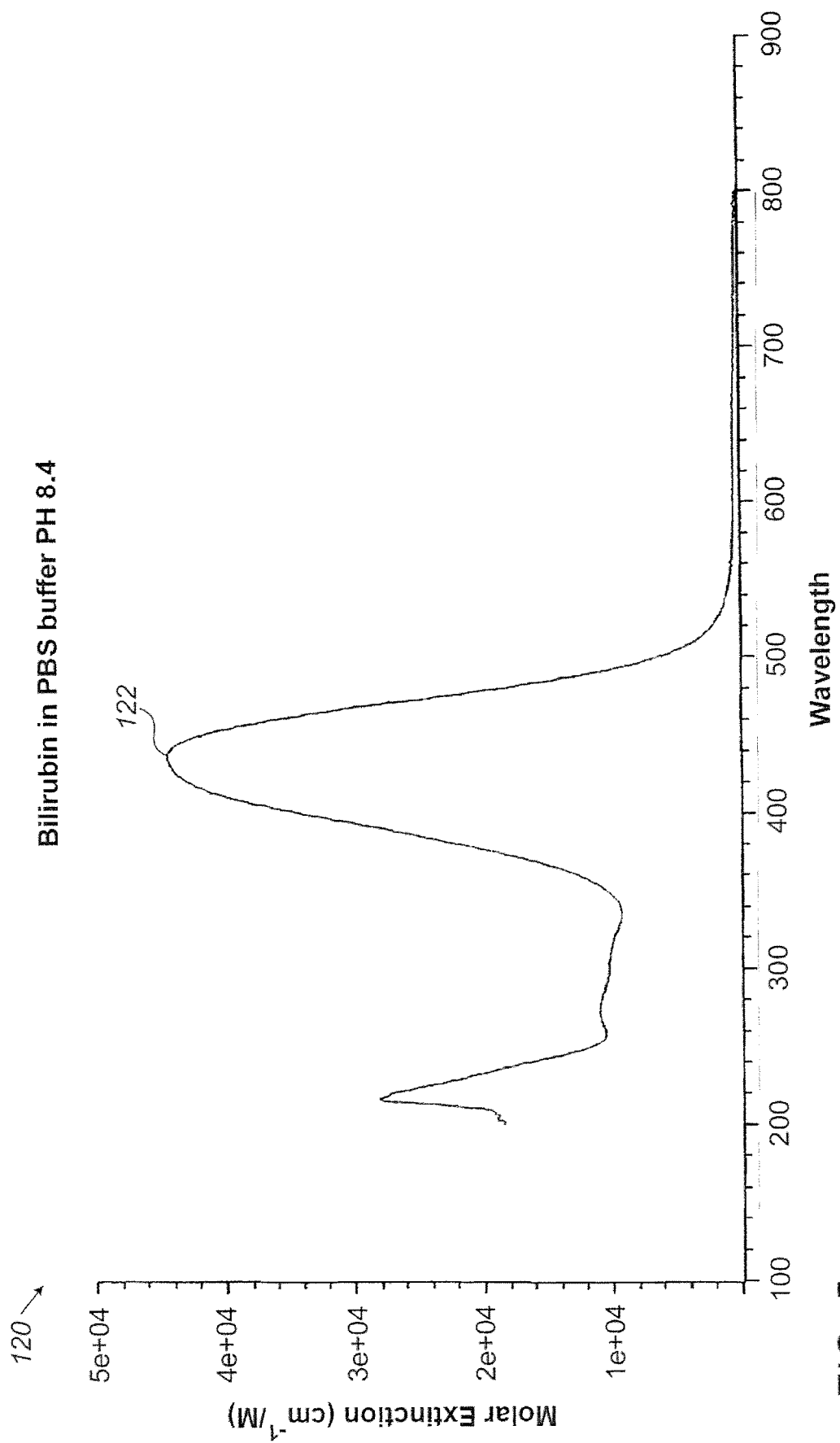
FIG. 5 schematically illustrates an absorption spectrum of bilirubin in a phosphate buffered saline (PBS) solution.

FIG. 5 schematically illustrates an absorption spectrum 120 of bilirubin in a phosphate buffered saline (PBS) solution. The absorption values were collected using a spectral bandwidth of 1.0 nm, a signal averaging time of 0.133 sec, a data interval of 0.25 nm, and a scan rate of 112.5 nm/min. These measurements were scaled to make the molar extinction coefficient match the value of 45,000 $cm^{-1}/M$ at 450.8 nm in chloroform at a marker 122 on absorption spectrum 120. Absorption spectrum 120 illustrates that absorption levels are significant in the range of 350 nm-510 nm with a peak absorption at 450.8 nm at marker 122.

Figure 6:
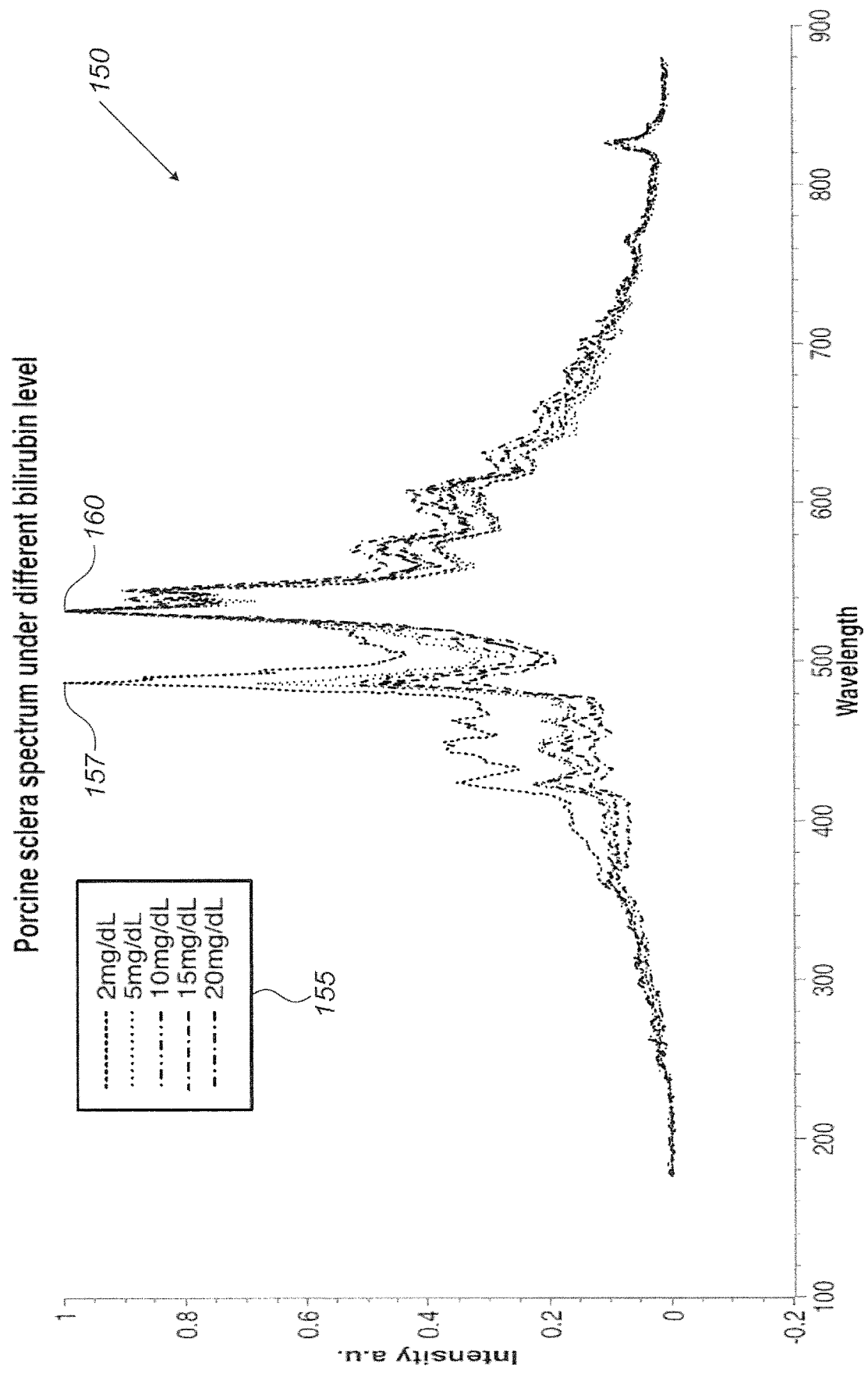
FIG. 6 schematically illustrates a porcine sclera spectrum for different bilirubin concentration levels, in accordance with some embodiments of the present disclosure.

FIG. 6 schematically illustrates a porcine sclera spectrum 150 for different bilirubin concentration levels 155, in accordance with some embodiments of the present disclosure. The overlay of the spectrum for different bilirubin concentration levels were normalized to the highest intensity value at 531 nm at a marker 160. Bilirubin concentration levels of 2 mg/dL, 5 mg/dL, 10 mg/dL, 15 mg/dL, and 20 mg/dL were used in the measurements. Spectrum 150 illustrates the relationship between the bilirubin concentration level and the reflectance data (e.g. shown in intensity in arbitrary units). Increasing bilirubin concentration levels may result in a drop of the signal from 350 nm to 510 nm with a peak at marker 157, which matches the bilirubin absorption spectrum.

In some embodiments of the present disclosure, a method of reflection photometry is used. Incident light may be directed onto sclera 50 in region 55. The reflected light may be collected in the at least one detector and the intensity of the reflected light may be measured. In the presence of bilirubin, the intensity may be reduced.

The light source may operate at wavelengths in the range of 400 m and 500 nm, and a light source at a wavelength of 531 nm may be used as a reference. The reference wavelength may be selected from a wavelength at which the reflectance is not impacted by the bilirubin concentration. Subsequently, the measurement wavelength for assessing bilirubin concentration levels may be selected from a wavelength at which the reflectivity varies with bilirubin concentration as shown at marker 157 in FIG. 6.

With the increase of the bilirubin concentration in the blood, the absorption of 400 nm-500 nm will increase resulting in a decrease in the intensity of reflected light. However, the variation of reference signal (e.g., at 531 nm) may only vary slightly due to the distance and angle from the sensor to the eye. The at least one detector may detect the signal reflected back from the sclera. Processor 70 and/or processor 101 may use the signal intensity data from the at least one detector in wavelength range from 400 nm-500 nm as bilirubin absorbance signal, and the signal intensity above 530 nm as the reference signal.

Figure 7A:
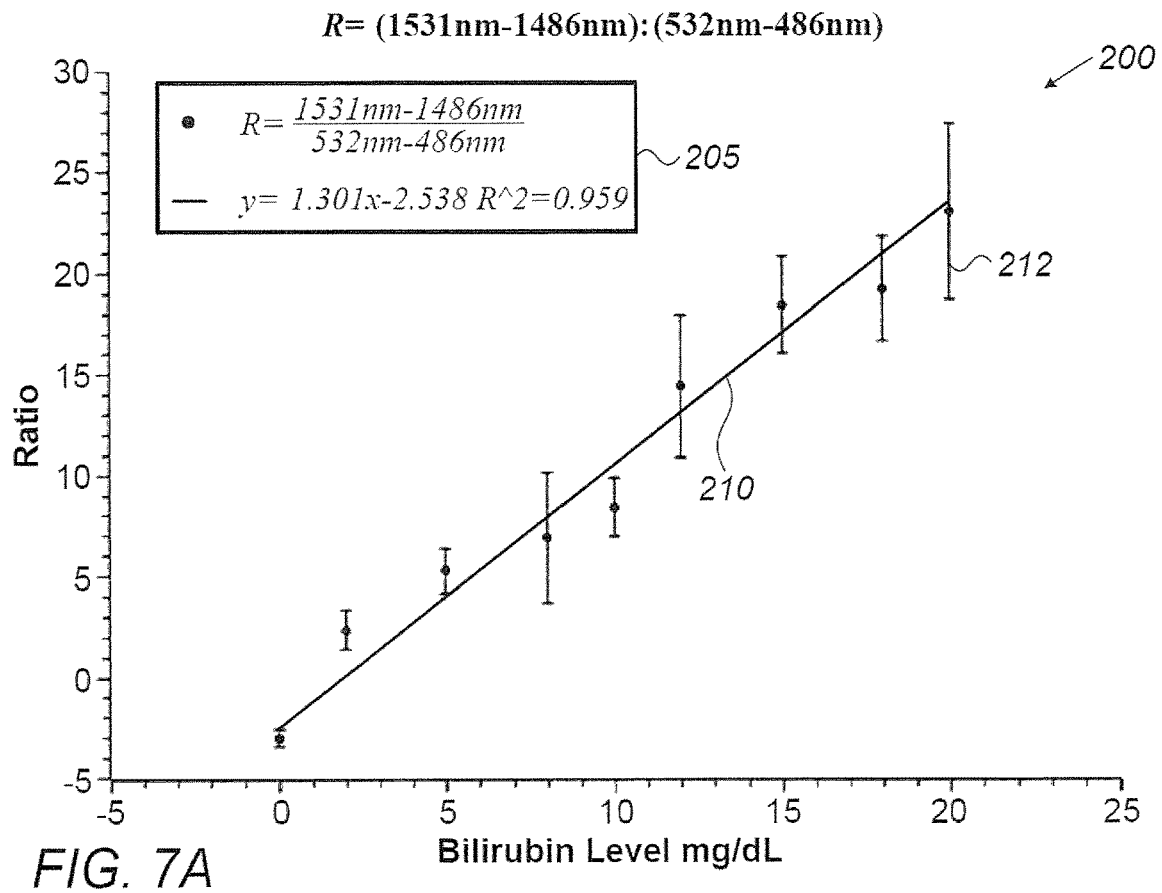
FIG. 7A schematically illustrates a first ratio of reflected to incident light intensities versus bilirubin concentration level, in accordance with some embodiments of the present so disclosure.

FIG. 7A schematically illustrates a first ratio of reflected to incident light intensities versus bilirubin concentration level, in accordance with some embodiments of the present disclosure.

Figure 7B:
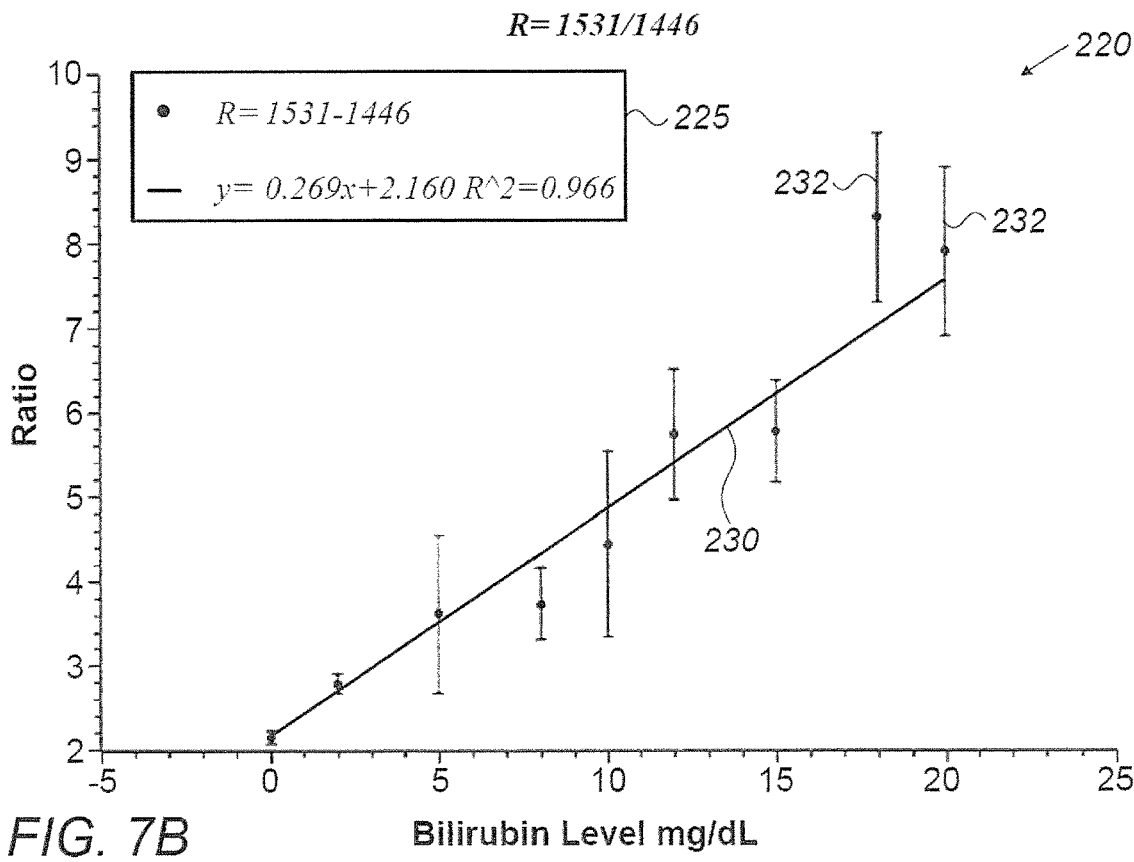
FIG. 7B schematically illustrates a second ratio of reflected to incident light intensities versus bilirubin concentration level, in accordance with some embodiments of the present disclosure.

FIG. 7B schematically illustrates a second ratio of reflected to incident light intensities versus bilirubin concentration level, in accordance with some embodiments of the present disclosure.

In some embodiments of the present disclosure, processor 70 and/or processor 101 may apply different algorithms to compute a ratio which may be used to analyze the bilirubin concentration level in the blood of a subject. For example:

(1) Ratio #1=(Intensity531 nm−Intensity486 nm)/(Intensity532 nm−Intensity486 nm) as shown in FIG. 7A.
(2) Ratio #2=(Intensity531 nm−Intensity502 nm)/(Intensity486 nm−Intensity502 nm).
(3) Ratio #3=Intensity531 nm/Intensity446 nm as shown in FIG. 7B.

Each of these three ratios have correlations R2>0.90. Thus, these ratios may be used to determine bilirubin concentration levels in optical sensor device 10 for quantifying jaundice based on the color of sclera 50. The three ratios shown above are not by way of limitation of the embodiments of the present disclosure. Any suitable ratio may be used.

In some embodiments of the present disclosure, the method of fluorescence emission by bilirubin may be used to determine the bilirubin concentration in the blood of the subject. In this case, incident light directed onto region 55 of sclera 50 may be used to excite bilirubin molecules. The emitted fluorescent light may be collected in the at least one detector and the intensity measured. In the presence of bilirubin, the measured intensity may increase. Optical sensor device 10 may use the measurement of the emitted fluorescence light in this manner to increase the flexibility and robustness of the detection system.

The at least one detector may include fluorescence detector such as a filtered photodiode with a range of 500-600 nm, a spectrometer, or camera. The received light in the at least one detector, for example a filtered photodiode or a spectrometer, may include fluorescence emission from the bilirubin in the sclera in a range of 500-600 nm.

In some embodiments of the present disclosure, the intensity measurements of the emitted fluorescence light may not be limited to sclera measurements since these measurements may not be affected by skin pigmentation, hemoglobin levels, melanin interference of the reflection detection mode on the skin. Accordingly, the intensity measurements of the emitted fluorescence light may be made at any suitable location on a body of the subject, such as the skin from the sternum, forehead, hand, gums and/or ear. These locations on the body may also minimize the effect of other tissue reflections like from the eyelids and the iris.

The quantification of the bilirubin concentration using the fluorescent emission signals may be more precise. Therefore, the estimation of bilirubin levels may become easier to implement. This approach may be used in optical sensor device 10 separately or together with the reflection method as described previously above. Both types of measurements may be performed on the sclera, on the skin, and/or on the gums of the subject.

Figure 8:
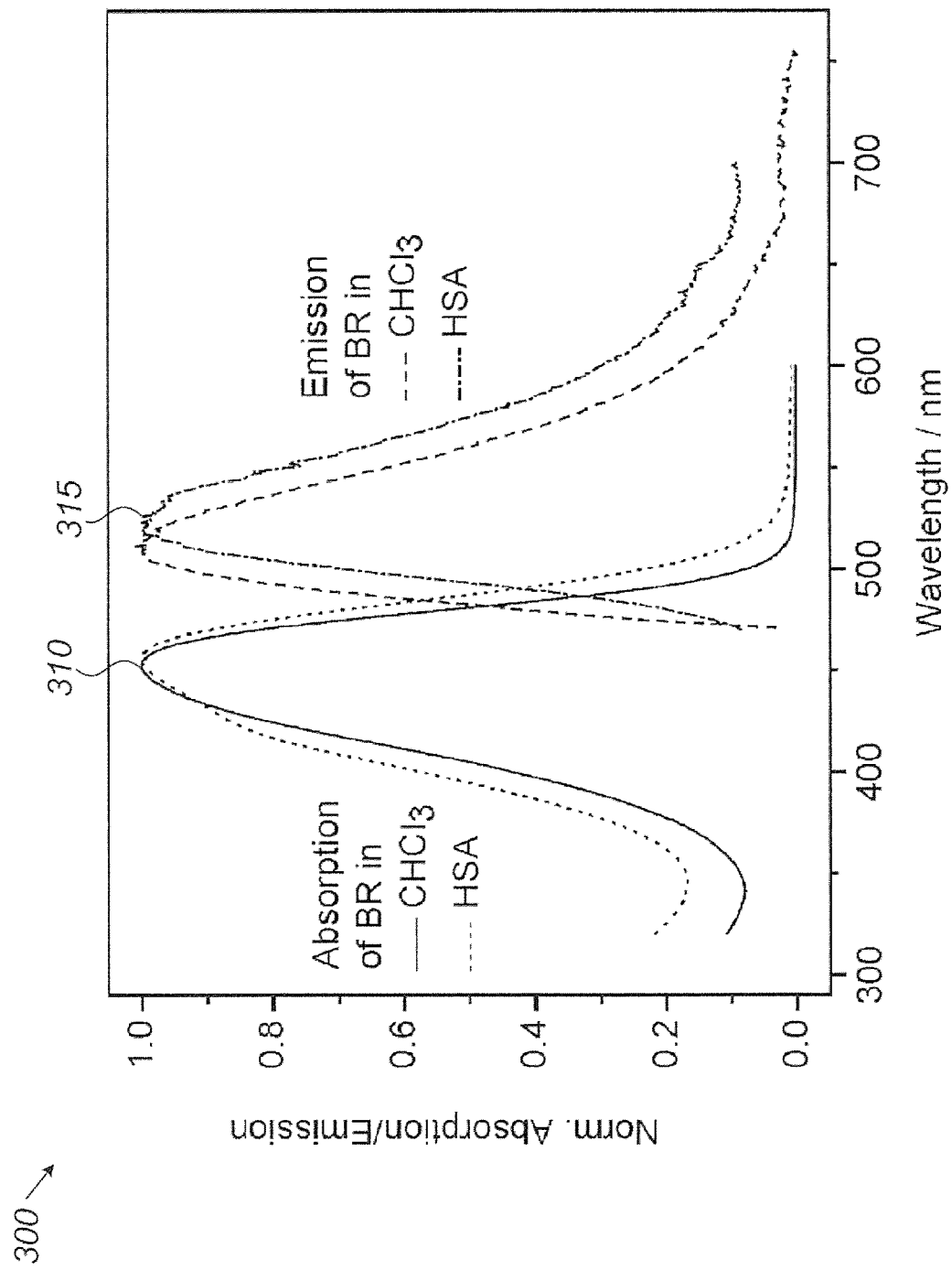
FIG. 8 schematically illustrates a graph of the normalized absorption and emission spectrum of bilirubin, in accordance with some embodiments of the present disclosure, and FIG. 9 schematically illustrates a graph of an analog-to-digital (ADC) converter output value versus bilirubin concentration level for fluorescence emission measurements from the sclera, in accordance with some embodiments of the present disclosure.

FIG. 8 schematically illustrates a graph 300 of the normalized absorption and emission spectrum of bilirubin, in accordance with some embodiments of the present disclosure. FIG. 8 shows the absorption and emission spectra of bilirubin (BR) in $CHCl_3$ and in phosphate buffered, human serum albumin (HSA) with pH 7.4. Bilirubin exhibits absorption from 380 nm to 500 nm with a peak excitation of 454 nm at a marker 310 and exhibits emission from 500 nm to 600 nm with a peak emission at 525 nm as shown by marker 315. Optical sensor device 10 may be configured to use all these wavelengths.

For example, a LED light source at 475±25 nm may be used as an excitation source. A detector with a cutoff at above 510 nm or with a detection range between 500 nm and 600 nm may be used to detect the emission light. The excitation light may be blocked using a band pass filter or a low pass filter, which transmits wavelengths longer than the excitation wavelength. Environmental light may be blocked from reaching the detector, or the measurement may be corrected for environmental light.

Another light source with a wavelength within the detector range may be applied to eye 20 to be used as a reference signal.

Figure 9:
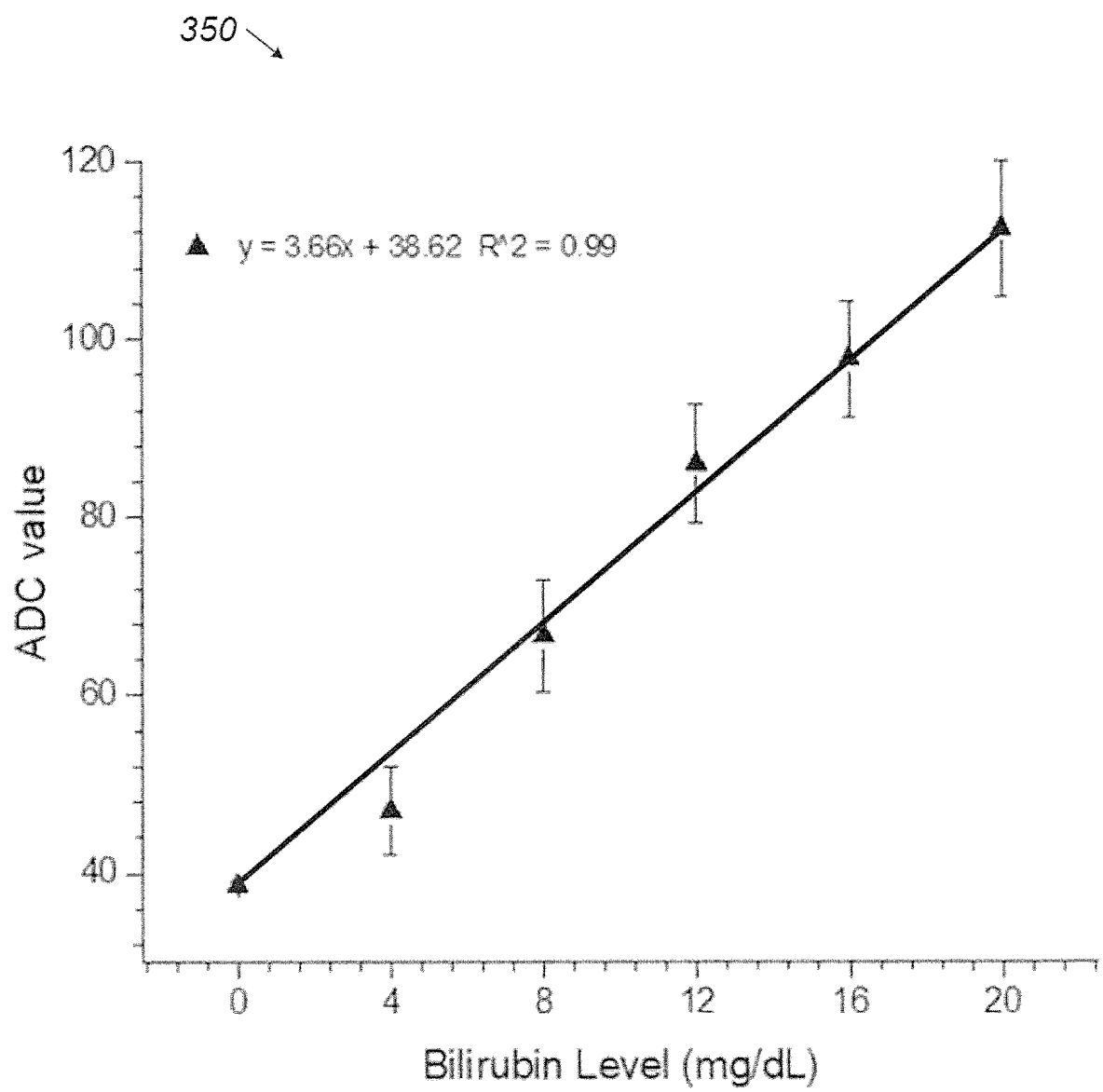

FIG. 9 schematically illustrates a graph 350 of an analog-to-digital (ADC) converter output value versus bilirubin concentration level for fluorescence emission measurements from the sclera, in accordance with some embodiments of the present disclosure. The ADC output value from ADC circuit 95 may be proportional to the measured intensity of fluorescence emission on the sclera of porcine eyes. Porcine eyes were incubated in bilirubin solutions with bilirubin concentrations of 0, 4, 8, 12, 16, 20 mg/dL for 24 hours. Fluorescent emission data was measured in a detector at a fixed distance of 3 mm from the sclera of the porcine eye. The data reveals in increase in the intensity fluorescent emission as a function of bilirubin concentration. No reference light source was used here.

In some embodiments of the present disclosure, a noninvasive optical sensor device for analyzing a level of a substance in a subject by illuminating a sclera, the optical sensor may include at least one light source, at least one detector, and a processor. The at least one light source may direct incident light to illuminate a region of a sclera of an eye of a subject. The at least one detector may receive light, in response to the incident light, from the sclera or from inside the eye proximal to the illuminated region of the sclera. The processor may be configured to compute a ratio of an intensity of the received light from the at least one detector to a reference value and to analyze a level of a substance in the subject from the computed ratio.

Ratio as used in herein may be functionally related to the received light intensity or power level and/or the incident light intensity or power level and/or frequency or wavelength of light and/or a band of wavelengths or frequencies of light and/or ADC value (e.g., from A/D 95) indicative of light intensity detected by the at least one detector. Reference value as used herein may be functionally related to the incident light intensity or power and/or light wavelengths and/or any suitable factor for normalizing the ratio, for example. Both the ratio and/or the reference value may include any correction factors for ambient light, for example.

As illustrated in FIGS. 7A and 7B and FIG. 9 map the ratio (e.g., intensity metrics) to the level of the substance in the blood (e.g., bilirubin concentration level). Memory 72 and/or memory 103 may include lookup table mappings between the computed ratio to the level of the substance in the blood of the subject, (e.g., for analyzing the level of the substance in the blood of the subject from the computed ratio).

In some embodiments of the present disclosure, the received light may include reflected light from the sclera or from inside the eye proximal to the illuminated region of the sclera.

In some embodiments of the present disclosure, the level of the substance may be the level of the substance in the blood of the subject.

In some embodiments of the present disclosure, the received light may include light emitted by fluorescence from tissue excited by the incident light from the sclera or from inside the eye proximal to the illuminated region of the sclera.

In some embodiments of the present disclosure, the optical sensor device may include optics for focusing the incident light onto the region of the sclera.

In some embodiments of the present disclosure, the optics may be configured to autofocus the incident light onto the region of the sclera.

In some embodiments of the present disclosure, the optical sensor device may include a communication module for relaying data to a remote communication device.

In some embodiments of the present disclosure, the communication module may include a Bluetooth module or a Wireless Fidelity (WiFi) module.

In some embodiments of the present disclosure, the processor is located on the remote mobile device and may be configured to use the relayed data so as to compute the ratio on the remote communication device.

In some embodiments of the present disclosure, the at least one light source may be selected from the group consisting of a xenon flash lamp, a light emitting diode, a laser diode, and a polychromatic light source with a bandpass filter.

In some embodiments of the present disclosure, the at least one detector may be selected from the group consisting of a photodiode, a photomultiplier tube, a photoresistor, a charge coupled device (CCD) sensor, a complementary metal-oxide semiconductor (CMOS) sensor, a fluorescence detector, a filtered photodiode, a spectrometer, and a camera.

In some embodiments of the present disclosure, the at least one light source emits pulsed light.

In some embodiments of the present disclosure, the level of the substance may include the concentration level of bilirubin in the blood.

In some embodiments of the present disclosure, the incident light directed to the region of the sclera for analyzing the concentration level of bilirubin may include light from the at least one light source with optical wavelengths in a range of 400 nm to 500 nm. The received light in the at least one detector may include reflected light from the eye in said range.

In some embodiments of the present disclosure, the incident light directed to the region of the sclera for analyzing the concentration level of bilirubin may include light from the at least one light source with optical wavelengths in a range of 380 nm to 500 nm. The received light in the at least one detector may include light emitted by fluorescence from the eye with optical wavelengths in a range of 500 nm to 600 nm.

In some embodiments of the present disclosure, the processor may be configured to assess that the subject has jaundice when the analyzed concentration level of bilirubin in the blood exceeds a predefined threshold.

In some embodiments of the present disclosure, a reagent is first injected into the eye of the subject. The reagent may be a dye, or a fluorescent labeled antibody, or a DNA, or methylene blue, or a methylene blue derivative, or a reagent binding to protein aggregates, or a reagent binding to the Tau protein, a fluorescent probe, or another reagent that interacts with a target molecule in the eye causing an optical change, such an absorbance change or fluorescent signal detectable by the optical device of the present disclosure. The reagent, e.g. a Fluorescence Resonance Energy Transfer (FRET) based binding reagent against Interleukin-6, is first injected into the eye, and is allowed to bind with its target interleukin-6 causing a separation of the quencher from the reporter dyes, which results in an increased fluorescence of the interleukin-6 reagent complex upon excitation with a suitable wavelength. The optical sensor device as described may then be used to detect the quantity of interleukin-6 reagent complex and thereby analyzing the interleukin-6 level. The analysis of interleukin-6 in the eye serves as a non-limiting example and similar homogeneous assays may be used for other cytokines, grows factors or biomarkers. An example is the Homogeneous Time Resolved Fluorescence (HTRF) assay based on two antibodies against the same target in which one antibody is conjugated with a quencher and the other antibody is conjugated with a reporter fluorophore. Such assays may be designed for all types of proteins, including protein aggregates.

By using a reagent specific to aggregated proteins in the eye, the aggregation level of proteins may be determined. This type of aggregation assay may be used to detect certain neurodegeneration deceases such as Alzheimer and Parkinson at an earlier stage.

In general, the device and method of the present disclosure may be used on either eye or on both eyes of the subject. Readings from both eyes of the subject may be taken and averaged to improve the accuracy of the determination of the substance.

In some embodiments of the present disclosure, a method for analyzing a level of a substance in the blood of a subject by illuminating a sclera with a noninvasive optical sensor device may include directing incident light from at least one light source to illuminate a region of a sclera of an eye of a subject. Light in at least one detector may be received, in response to the incident light, from the sclera or from inside the eye proximal to the illuminated region of the sclera. A ratio of an intensity of the received light from the at least one detector to a reference value may be computed. A level of a substance in the blood of the subject may be analyzed from the computed ratio.

Some embodiments of the present disclosure may include a system, a method, and/or a computer program product. The computer program product may include a tangible non-transitory computer readable storage medium (or media) having computer readable program instructions thereon for causing a processor to carry out aspects of the present disclosure. Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including any object oriented programming language and/or conventional procedural programming languages.

Before explaining at least one embodiment of the disclosure in detail, it is to be understood that the disclosure is not necessarily limited in its application to the details of construction and the arrangement of the components and/or methods set forth in the following description and/or illustrated in the drawings and/or the Examples. The disclosure is capable of other embodiments or of being practiced or carried out in various ways.

In the context of some embodiments of the present disclosure, by way of example and without limiting, terms such as 'operating' or 'executing' imply also capabilities, such as 'operable' or 'executable', respectively.

Conjugated terms such as, by way of example, 'a thing property' implies a property of the thing, unless otherwise clearly evident from the context thereof.

The terms 'processor' or 'computer', or system thereof, are used herein as ordinary context of the art, such as a general purpose processor, or a portable device such as a smart phone or a tablet computer, or a micro-processor, or a RISC processor, or a DSP, possibly comprising additional elements such as memory or communication ports. Optionally or additionally, the terms 'processor' or 'computer' or derivatives thereof denote an apparatus that is capable of carrying out a provided or an incorporated program and/or is capable of controlling and/or accessing data storage apparatus and/or other apparatus such as input and output ports. The terms 'processor' or 'computer' denote also a plurality of processors or computers connected, and/or linked and/or otherwise communicating, possibly sharing one or more other resources such as a memory.

The terms 'software', 'program', 'software procedure' or 'procedure' or 'software code' or 'code' or 'application' may be used interchangeably according to the context thereof and denote one or more instructions or directives or electronic circuitry for performing a sequence of operations that generally represent an algorithm and/or other process or method. The program is stored in or on a medium such as RAM, ROM, or disk, or embedded in a circuitry accessible and executable by an apparatus such as a processor or other circuitry. The processor and program may constitute the same apparatus, at least partially, such as an array of electronic gates, such as FPGA or ASIC, designed to perform a programmed sequence of operations, optionally comprising or linked with a processor or other circuitry.

The term 'configuring' and/or 'adapting' for an objective, or a variation thereof, implies using at least a software and/or electronic circuit and/or auxiliary apparatus designed and/or implemented and/or operable or operative to achieve the objective.

A device storing and/or comprising a program and/or data constitutes an article of manufacture. Unless otherwise specified, the program and/or data are stored in or on a non-transitory medium.

In case electrical or electronic equipment is disclosed it is assumed that an appropriate power supply is used for the operation thereof.

The block diagrams illustrate architecture, functionality or an operation of possible implementations of systems, methods and computer program products according to various embodiments of the present disclosed subject matter. In this regard, each block in the flowchart or block diagrams may represent a module, segment, or portion of program code, which comprises one or more executable instructions for implementing the specified logical function(s). It should also be noted that, in some alternative implementations, illustrated or described operations may occur in a different order or in combination or as concurrent operations instead of sequential operations to achieve the same or equivalent effect.

The corresponding structures, materials, acts, and equivalents of all means or step plus function elements in the claims below are intended to include any structure, material, or act for performing the function in combination with other claimed elements as specifically claimed. As used herein, the singular forms "a", "an" and "the" are intended to include the plural forms as well, unless the context clearly indicates otherwise. It will be further understood that the terms "comprising", "including" and/or "having" and other conjugations of these terms, when used in this specification, specify the presence of stated features, integers, steps, operations, elements, and/or components, but do not preclude the presence or addition of one or more other features, integers, steps, operations, elements, components, and/or groups thereof.

The terminology used herein should not be understood as limiting, unless otherwise specified, and is for the purpose of describing particular embodiments only and is not intended to be limiting of the disclosed subject matter. While certain embodiments of the disclosed subject matter have been illustrated and described, it will be clear that the disclosure is not limited to the embodiments described herein. Numerous modifications, changes, variations, substitutions and equivalents are not precluded.

The invention claimed is:

1. An optical sensor device for analyzing a level of a substance of a subject by illuminating a sclera, the optical sensor device comprising:
   at least one light source for directing incident light to illuminate a region of a sclera of an eye of a subject;
   optics configured to autofocus the incident light onto the region of the sclera;
   at least one detector for receiving light, in response to the incident light, from the sclera or from inside the eye proximal to the illuminated region of the sclera; and
   a processor configured to compute a ratio of intensity of the received light from the at least one detector to a reference signal and to analyze a level of a substance in the subject from the computed ratio.

2. The optical sensor device according to claim 1, wherein the received light comprises reflected light from the sclera or from inside the eye proximal to the illuminated region of the sclera.

3. The optical sensor device according to claim 1, wherein the level of the substance is the level of the substance in the blood of the subject.

4. The optical sensor device according to claim 1, wherein the received light comprises light emitted by fluorescence from tissue, a substance, or a reagent excited by the incident light from the sclera or from inside the eye proximal to the illuminated region of the sclera.

5. The optical sensor device according to claim 1, further comprising a communication module for relaying data to a remote mobile device.

6. The optical sensor device according to claim 5, wherein the communication module comprises a Bluetooth module or a Wireless Fidelity (WiFi) module.

7. The optical sensor device according to claim 5, wherein the processor is located on the remote mobile device and configured to use the relayed data so as to compute the ratio on the remote mobile device.

8. The optical sensor device according to claim 1, wherein the at least one light source is selected from the group consisting of a xenon flash lamp, a light emitting diode, a laser diode, and a polychromatic light source with a bandpass filter.

9. The optical sensor device according to claim 1, wherein the at least one detector is selected from the group consisting of a photodiode, a photomultiplier tube, a photoresistor, a charge coupled device (CCD) sensor, a complementary metal-oxide semiconductor (CMOS) sensor, a fluorescence detector, a filtered photodiode, a spectrometer, and a camera.

10. The optical sensor device according to claim 1, wherein the at least one light source emits a pulsed light.

11. The optical sensor device according to claim 1, wherein the level of the substance comprises concentration level of bilirubin in the blood.

12. The optical sensor device according to claim 11, wherein the incident light directed to the region of the sclera for analyzing the concentration level of bilirubin comprises light from the at least one light source with a wavelength in a range of 400 nm to 500 nm, and wherein the received light in the at least one detector comprises reflected light from the eye in said range.

13. The optical sensor device according to claim 11, wherein the incident light directed to the region of the sclera for analyzing the concentration level of bilirubin comprises light from the at least one light source with a wavelength in a range of 380 nm to 500 nm, and wherein the received light in the at least one detector comprises light emitted by fluorescence from the eye with a wavelength in a range of 500 nm to 600 nm.

14. The optical sensor device according to claim 11, wherein the processor is configured to assess that the subject has jaundice when the concentration level of bilirubin in the blood exceeds a predefined threshold.

15. A method for analyzing a level of bilirubin in the blood of a subject by illuminating a sclera using a noninvasive optical sensor device, the method comprising the steps of:

directing incident light having a wavelength in a range from 380 nm to 500 nm from at least one light source to illuminate a region of a sclera of an eye of a subject;

receiving light emitted by fluorescence with a wavelength in a range from 500 nm to 600 nm in at least one detector in response to the incident light, from the sclera or from inside the eye proximal to the illuminated region of the sclera;

computing a ratio of an intensity of the received light from the at least one detector to a reference signal; and analyzing the level of bilirubin in the blood of the subject from the computed ratio.

16. The method according to claim 15, wherein directing the incident light to the region of the sclera for analyzing the concentration level of bilirabin comprises directing light from the at least one light source with a wavelength in a range of 400 nm 500 nm.

17. The method according to claim 15, further comprising assessing that the subject has jaundice when the analyzed concentration level of bilirubin in the blood exceeds a predefined threshold.

* * * * *